(12) United States Patent
Guo et al.

(10) Patent No.: US 7,257,279 B2
(45) Date of Patent: Aug. 14, 2007

(54) SYSTEMS AND METHODS FOR BIOSENSING AND MICRORESONATOR SENSORS FOR SAME

(75) Inventors: Chunmei Guo, Woodbury, MN (US); Xudong Fan, Columbia, MO (US)

(73) Assignee: 3M Innovative Properties Company, St. Paul, MN (US)

( * ) Notice: Subject to any disclaimer, the term of this patent is extended or adjusted under 35 U.S.C. 154(b) by 65 days.

(21) Appl. No.: 10/945,327

(22) Filed: Sep. 20, 2004

(65) Prior Publication Data

US 2006/0062508 A1 Mar. 23, 2006

(51) Int. Cl.
G02B 6/42 (2006.01)
G02B 6/00 (2006.01)
G02B 6/26 (2006.01)

(52) U.S. Cl. ............................. 385/12; 385/31; 385/32
(58) Field of Classification Search .................... None
See application file for complete search history.

(56) References Cited

U.S. PATENT DOCUMENTS

| | | | |
|---|---|---|---|
| 3,833,284 | A | 9/1974 | Kaminow et al. |
| 4,715,672 | A | 12/1987 | Duguay et al. |
| 5,077,822 | A | 12/1991 | Cremer |
| 6,389,197 | B1 | 5/2002 | Iltchenko et al. |
| 6,490,039 | B2 | 12/2002 | Maleki et al. |
| 6,507,684 | B2 | 1/2003 | Tapalian et al. |
| 6,512,866 | B1 | 1/2003 | Fan et al. |
| 6,583,399 | B1 | 6/2003 | Hunziker et al. |
| 6,594,425 | B2 | 7/2003 | Tapalian et al. |
| 6,657,731 | B2 | 12/2003 | Tapalian et al. |
| 6,668,111 | B2 | 12/2003 | Tapalian et al. |
| 6,781,696 | B1 | 8/2004 | Rosenberger et al. |
| 6,795,481 | B2 | 9/2004 | Maleki et al. |
| 6,865,317 | B2 | 3/2005 | Vahala et al. |

(Continued)

FOREIGN PATENT DOCUMENTS

GB 2 293 883 4/1996

(Continued)

OTHER PUBLICATIONS

U.S. Appl. entitled "Dielectric Microcavity Fluorosensors Excited with a Broadband Light Source" filed May 27, 2004, having U.S. Appl. No. 10/854,911.

(Continued)

*Primary Examiner*—Frank G. Font
*Assistant Examiner*—Eric Wong
(74) *Attorney, Agent, or Firm*—Stephen W. Buckingham

(57) ABSTRACT

A biosensor system is provided for detecting biological species such as bacteria, proteins, viruses, spores and DNA or RNA. The biosensor system may also be able to distinguish between Gram positive and Gram negative bacteria. In some embodiments, the analyte solution flows past a detector surface to a filter, which traps the analyte. The analyte is then washed back past the detector surface, thus increasing the number of analyte species that become attached to the surface. The detector may include an optical microresonator that is optically coupled via waveguides to a light source and an optical detector. One of the waveguides may be provided with a wavelength selective reflector to increase the amount of probe light coupled into the microresonator or to increase the fraction of the signal light detected by the optical detector.

23 Claims, 5 Drawing Sheets

U.S. PATENT DOCUMENTS

| | | | |
|---|---|---|---|
| 6,888,987 B2 | 5/2005 | Sercel et al. | |
| 6,891,996 B2 | 5/2005 | Sercel et al. | |
| 6,891,997 B2 | 5/2005 | Sercel et al. | |
| 6,895,135 B2 | 5/2005 | Kaneko et al. | |
| 6,901,101 B2* | 5/2005 | Frick | 372/92 |
| 2002/0018611 A1 | 2/2002 | Maleki et al. | |
| 2002/0041730 A1 | 4/2002 | Sercel et al. | |
| 2002/0044739 A1 | 4/2002 | Vahala et al. | |
| 2002/0068018 A1 | 6/2002 | Pepper et al. | |
| 2002/0079453 A1 | 6/2002 | Tapalian et al. | |
| 2002/0094150 A1 | 7/2002 | Lim et al. | |
| 2002/0097401 A1 | 7/2002 | Maleki et al. | |
| 2002/0172457 A1 | 11/2002 | Tapalian et al. | |
| 2002/0192680 A1 | 12/2002 | Chan et al. | |
| 2003/0082237 A1 | 5/2003 | Cha et al. | |
| 2004/0023396 A1 | 2/2004 | Boyd et al. | |
| 2004/0091212 A1 | 5/2004 | Strecker et al. | |
| 2004/0120638 A1* | 6/2004 | Frick | 385/27 |
| 2004/0146431 A1* | 7/2004 | Scherer et al. | 422/82.05 |
| 2004/0196465 A1 | 10/2004 | Arnold et al. | |
| 2005/0035278 A1* | 2/2005 | Margalit et al. | 250/227.14 |
| 2005/0077513 A1 | 4/2005 | Fan et al. | |
| 2005/0078731 A1 | 4/2005 | Fan et al. | |
| 2005/0105868 A1 | 5/2005 | Arakida | |
| 2005/0111309 A1 | 5/2005 | Peng | |
| 2005/0147372 A1 | 7/2005 | Bourdelais et al. | |
| 2005/0265658 A1 | 12/2005 | Fan et al. | |

FOREIGN PATENT DOCUMENTS

| | | |
|---|---|---|
| GB | 2 387 130 | 10/2003 |
| WO | WO 01/40757 A2 | 6/2001 |
| WO | WO 01/67565 A1 | 9/2001 |
| WO | 01/85341 | 11/2001 |
| WO | WO 02/13337 A1 | 2/2002 |
| WO | WO 02/16986 A1 | 2/2002 |
| WO | WO 2004/038370 A2 | 5/2004 |

OTHER PUBLICATIONS

Pettipher, G.L., et al; "Rapid Enumeration of Microorganisms in Foods by the Direct Epifluorescent Filter Technique", *Applied and Environmental Microbiology* (Oct. 1982); vol. 44, No. 4; pp. 809-813.

Luk, J.M.C., et al; "Rapid and Sensitive Detection of *Salmonella* (O : 6,7) by Immunomagnetic Monoclonal Antibody-Based Assays", *Journal of Immunological Methods* (1991); vol. 137; pp. 1-8.

Tortorello, M.L., et al; "Antibody-Direct Epifluorescent Filter Technique for Rapid, Direct Enumeration of *Escherichia coli* O157:H7 in Beef", *Applied and Environmental Microbiology* (Oct. 1994); vol. 60, No. 10; pp. 3553-3559.

Tortorello, M.L., et al; "Rapid Identification of *Escherichia coli* O157:H7 in Bovine Feces Using the Antibody-Direct Epifluorescent Filter Technique (Ab-DEFT)", *Veterinary Microbiology* (1996); vol. 51; pp. 343-349.

Popescu, A., et al; "The Gram Stain after More than a Century", *Biotechnic and Histochemistry* (1996); vol. 71, No. 3; pp. 145-151.

Plowman, T.E., et al; "Femtomolar Sensitivity Using a Channel-Etched Thin Film Waveguide Fluoroimmunsensor", *Biosensors & Bioelectronics* (1996); Elsevier Science Ltd.; vol. 11, No. 1/2; pp. 149-160.

Xu, G.; "Gram Stain"; University of Pennsylvania Health System [on line]; [available on the internet on Oct. 31, 1997]; [retrieved from the internet on Dec. 15, 2004]; URL <http://www.uphs.upenn.edu/bugdrug/antibiotic_manual/gram.htm>; pp. 10.

Vernooy, D.W., et al; "High-Q Measurement of Fused-Silica Micropsphers in the Near Infrared", *Optics Letter* (Feb. 15, 1998); vol. 23, No. 4; pp. 247-249.

Krioukov, E., et al; "Integrated Optical Microcavities for Enhanced Evanescent-Wave Spectroscopy", *Optics Letters* (Sep. 1, 2002); vol. 27, No. 17; pp. 1504-1506.

Garmire, E., et al., "Propagation Losses in Metal-Film-Subtrate Optical Waveguides," *Journal of Quantum Electronics*, vol. QE-8, No. 10, Oct. 1972, pp. 763-766.

Kaminow, I.P., et al., "Metal-Clad Optical Waveguides: Analytical and Experimental Study," *Applied Optics*, vol. 13, No. 2, Feb. 1974, pp. 396-405.

Otto, A., et al., "Modification of the Total Reflection Modes in a Dielectric Film by One Metal Boundary," *Optics Communications*, vol. 3, No. 4, Jun. 1971, pp. 254-258.

Reisinger, A., "Attenuation Properties of Optical Waveguides with a Metal Boundary," *Appl. Phys. Lett.*, vol. 23, No. 5, Sep. 1, 1973, pp. 237-239.

Suematsu, et al., "Fundamental Transverse Electric Field (TEo) Mode Selection for Thin-Film Asymmetric Light Guides," *Appl. Phys. Lett.*, vol. 21, No. 6, Sep. 15, 1972, pp. 291-293.

Tien, P., et al., "Novel Metal-clad Optical Components and Method of Isolating High-Index Substrates for Forming Integrated Optical Circuits," *Appl. Phys. Lett.*, vol. 27, No. 4, Aug. 15, 1975, pp. 251-253.

Yoneyama et al., "Nonradiative Dielectric Waveguide Circuit Components" *International Journal of Infrared and Millimeter Waves*, vol. 4, No. 3, (1983), pp. 439-449.

Armani, D.K., et al; "Ultra-High-Q Toroid microcavity on a Chip", *Letters to Nature*, Nature (Feb. 27, 2003); vol. 421, Nature Publishing Group; pp. 925-928.

Blair et al., "Resonant-enhanced evanescent-wave fluorescence biosensing with cylindrical optical cavities", Applied Optics, vol. 40, No. 4, Feb. 1, 2001, pp. 570-582.

Boyd et al., "Sensitive disk resonator photonic biosensor", Applied Optics, vol. 40, No. 31, Nov. 1, 2001, pp. 5742-5747.

Burlak, G., et al; "Electromagnetic Eigenoscillations and Fields in a Dielectric Microsphere with Multilayer Spherical Stack", *Optics Conmmunications* (Jan. 1, 2001); vol. 187, Elsevier Science B.V.; pp. 91-105.

Burlak, G., et al; "Electromagnetic Oscillations in a Multilayer Spherical Stack", *Optics Communications,* (Jun. 1, 2000); vol. 180; Elsevier Science B.V.; pp. 49-58.

Burlak, G., et al; "Transmittance and Resonance Tunneling of the Optical Fields in the Microspherical Metal-Dielectric Structures", *Optics Communications* (May 15, 2002); vol. 206, Elsevier Science B.V.; pp. 27-37.

Chan, S., et al; "Identification of Gram Negative Bacteria Using Nanoscale Siicon Microcavities", Communications to the Editor, *Journal of American Chemical Society* (Nov. 2001); vol. 123, pp. 11797-11798.

Chan, S., et al; "Nanoscale Silicon Microcavities for Biosensing", *Materials Science and Engineering C* (2001); vol. 15, Elsevier Science B.V.; pp. 277-282.

Coffer et al., "Strategies Toward the Development of Integrated Chemical Sensors Fabricated from Light Emitting Porous Silicon", Proceedings of the SPIE, vol. 3226, 1997, pp. 168-179.

Crisan et al., "Sol-Gel Preparation of Thin Films for Integrated Optics", 10th International Symposium on Electron Devices for Microwave and Optoelectronic Applications, Nov. 18-19, 2002, Manchester, UK., pp. 205-210.

Johnson, B.R.; "Theory of Morphology-Dependent Resonances: Shape Resonances and Width Formulas", *J. Opt. Soc. Am. A* (Feb. 1993); vol. 10, No. 2; pp. 343-352.

Kakarantzas, G., et al; "Miniature All-Fiber Devices Based on $CO_2$ Laser Microstructuring of Tapered Fibers", *Optics Letters* (Aug. 1, 2001); vol. 26, No. 15; pp. 1137-1139.

Knight, J.C., et al; "Mapping Whispering-Gallery Modes in Microspheres with a Near-Field Probe", *Optics Letters* (Jul. 15, 1995); vol. 20, No. 14; pp. 1515-1517.

Krioukov et al., "Sensor based on an integrated optical microcavity", Optics Letters, vol. 27, No. 7, Apr. 1, 2002, pp. 512-514.

Laine, J.-P., et al; "Acceleration Sensor Based on High-Q Optical Microsphere Resonator and Pedestal Antiresonant Reflecting Waveguide Coupler", *Sensors and Actuators A* (2001); vol. 93; Elsevier Science B.V.; pp. 1-7.

Laine, J.-P., et al; "Microsphere Resonator Mode Characterization by Pedestal Anti-Resonant Reflecting Waveguide Coupler", *IEEE Photonics Technology Letters* (Aug. 2000); vol. 12, No. 8; pp. 1004-1006.

Little, B.E., et al; "Pedestal Antiresonant Reflecting Waveguides for Robust Coupling to Microsphere Resonators and for Microphotonic Circuits", *Optics Letters* (Jan. 1, 2000); vol. 25, No. 1; pp. 73-75.

Lugo, J.E., et al; "Porous Silicon Multilayer Structures: A Photonic Band Gap Analysis", *Journal of Applied Physics* (Apr. 15, 2002); vol. 91, No. 8; pp. 4966-4972.

Martin, A.L., et al; "Replica-Molded High-Q Polymer Microresonators", *Optics Letters* (Mar. 15, 2004); vol. 29, No. 6; pp. 533-535.

Pipino et al; "Evanescent wave cavity ring-down spectroscopy with a total-internal-reflection minicavity", Review of Scientific Instruments, American Institute of Physics, vol. 68, No. 8, Aug. 8, 1997, pp. 2978-2989.

Shibata et al., "Laser Emission from Dye-Doped Organic-Inorganic Particles of Mircocavity Structure", Journal of Sol-Gel Science and Technology, vol. 8, 1997, pp. 959-964.

Spillane, S.M., et al; "Ultralow-Threshold Raman Laser Using a Spherical Dielectric Microcavity", Letters to Nature, *Nature* (Feb. 7, 2002); vol. 415, Macmillan Magazines Ltd.; pp. 621-623.

Sumetsky, M., "Whispering-Gallery-Bottle Microcavities: the Three-Dimensional Etalon", *Optics Letters* (Jan. 1, 2004); vol. 29, No. 1; pp. 8-10.

Tapalian, C., et al., "High-Q Silica Microsphere Optical Resonator Sensors Using Stripline-Pedestal Anti-Resonant Reflecting Optical Waveguide Couplers"; *Proceedings from SPIE, Photonics West 2003* (Jan. 25-31, 2003); vol. 4969; Laser Resonators and Beam Control VI; Item 4969-30; pp. 11-22.

Vollmer, F., et al; "Protein Detection by Optical Shift of a Resonant Microcavity", *Applied Physics Letters* (May 27, 2002); vol. 80, No. 21; pp. 4057-4059.

Wark et al., "Incorporation of organic dye molecules in nanoporous crystals for the development of hexgonal solid state microlasers", Proceedings of the SPIE, vol. 4456, 2001, pp. 57-67.

Yunfeng et al., "Chemical sensors based on hydrophobic porous sol-gel films and ATR-FTIR spectroscopy", Sensors and Actuators B, Elsevier Sequoia S.A., vol. B36, No. 1, 2, and 3, Oct. 1996, pp. 517-521.

Chan, S., et al. "Porous Silicon Microactivities for Biosensing Applications," *Physical Status Solid*, vol. 182, (2000) pp. 541-546.

De Stefano, L., et al., "Optical Sensing of Flammable Substances Using Porous Silicon Microactivities," *Materials Science and Engineering*, vol. 100, Jul. 25, 2003, pp. 271-274.

Mulloni, V., et al. "Porous Silicon Microactivites as Optical Chemical Sensors," *Applied Physics Letters*, vol. 76, No. 18, May 1, 2000, pp. 2523-2525.

International Search Report from Application No. PCT/US2005/029023, filed Aug. 15, 2005.

\* cited by examiner

— 3.dat, [Staph Aureaus] = 10^7 cells/ml
— non-specific binding

SYSTEMS AND METHODS FOR BIOSENSING AND MICRORESONATOR SENSORS FOR SAME

FIELD OF THE INVENTION

The invention is directed generally to systems and methods for detecting bacteria, including optical sensors that use microresonators.

BACKGROUND

The detection of biological species is an important analytical technique in several industries, including the food industry, environmental monitoring, and health care, e.g. for the prevention of post-surgical infection. For example, traditional methods of detecting bacteria require the culturing of microorganisms. While these methods provide a desired level of sensitivity, they require highly trained laboratory personnel and typically need days to obtain results.

Post-surgery infections constitute the most common infection for surgical patients. In many cases, bacteria still remain on the skin after the skin has been prepared for surgery. About 20% of the population have high bacteria counts on the skin, i.e. more than 1000 CFU $cm^{-2}$ and represent those who are at greatest risk of infection. Accordingly, microbial detection is particularly important when preparing these patients for surgery. The bacteria on the skin are typically of the Gram positive type, and so it is important to be able to distinguish Gram positive bacteria. In other health care situations, it is important to differentiate between Gram negative and Gram positive bacteria, and to detect the total bacterial number from skin, wound, and body fluid (e.g., urine) samples. It is important also to be able to detect bacteria from environmental samples taken from food processing and clinical settings. The types of bacteria in these samples are typically Gram negative. Gram negative bacteria can be detected at very low concentration with a stable limulus amoebocyte lysate (LAL) reagent. The chromogenic substrate (p-nitroaniline) supplied with the commercial LAL changes from colorless to yellow in the presence of lipopolysaccharide (LPS) and is readily measured in a spectrophotometer. LAL cannot, however, distinguish between bacteria-surface bound LPS and free (soluble) LPS in solution. Free LPS is present in most environmental samples. It is either released under normal bacterial growth processes or from the dead gram-negative bacteria. The separation of soluble LPS from intact bacteria is a very challenging issue.

SUMMARY OF THE INVENTION

There remains a need, therefore, for a method of detecting biological species, such as bacteria (both Gram positive and Gram negative), viruses, spores, proteins and DNA and RNA strands, that is sensitive, less expensive than conventional methods and produces results rapidly.

One embodiment of the invention is directed to a biosensor system that comprises a sensing chamber having an interior volume and a biosensor unit operatively coupled to the interior volume of the sensing chamber. A filter is disposed within the sensing chamber. The sensing chamber has an input to the sensing chamber for introducing an analyte solution into the sensing chamber. The input is arranged and configured so that at least some of the analyte solution interacts with the bacterial sensor unit before reaching the filter. In some embodiments, the biosensor unit may include an optical biosensor having an optical microcavity.

Another embodiment of the present invention is directed to a method of operating a biosensor. The method includes placing an analyte solution into a sensing chamber containing at least a surface of a biosensor and a filter, and washing the solution past at least a surface of the biosensor to a filter. At least some of the analyte is trapped at the filter. At least some of the trapped analyte is washed off the filter back towards the surface of the biosensor. The analyte on the surface of the biosensor is detected.

Another embodiment of the invention is directed to microresonator sensor apparatus that comprises a light source optically coupled to inject probe light into a probe waveguide. A microcavity resonator is optically coupled to the probe waveguide, at an input coupling region of the probe waveguide. The probe waveguide comprises a first probe light reflector so that light that propagates from the light source through the input coupling region of the probe waveguide without being coupled into the microcavity resonator is reflected back towards the input coupling region.

Another embodiment of the invention is directed to a microresonator sensor apparatus that comprises a light source to generate probe light and a microcavity resonator defining whispering gallery modes that is optically coupled to receive at least some of the probe light into at least one of the whispering gallery modes. The apparatus also comprises a detector unit and a signal waveguide optically coupled between the microcavity resonator and the detector unit. Signal light propagates from the microcavity resonator to the detector unit via the signal waveguide. The signal waveguide comprises a signal light reflector, reflective at the wavelength of the signal light. The signal light reflector is disposed to reflect signal light in the signal waveguide towards the detector unit.

The above summary of the present invention is not intended to describe each illustrated embodiment or every implementation of the present invention. The figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1A:
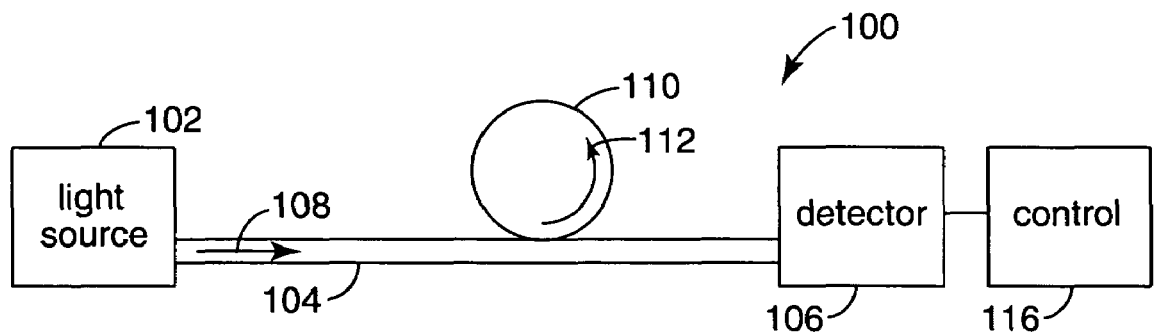
FIGS. 1A–1C schematically illustrate different embodiments of microcavity sensors according to principles of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is particularly applicable to microbial sensing using microcavity resonators. Such resonators may also be referred to as microresonators.

Optical biosensors offer a sensitive, rapid and cost-effective alternative to conventional microbial sensing techniques. A microsphere-based biosensor is one such type of optical biosensor, which relies on the whispering gallery modes (WGMs) that circulate inside the microsphere surface. Microspheres are typically made of fused silica and can be fabricated with a $CO_2$ laser or a flaming system. The typical size of a microsphere ranges from a few tens of microns to a few hundreds of microns in diameter. A microsphere does not have to be absolutely spherical in shape, and the term is used for a microcavity that provides optical confinement in three dimensions. This is intended to include bulge-like microcavities of the type discussed in commonly owned U.S. patent application Ser. No. 10/855,462, incorporated herein by reference. In contrast, flat or planar microcavities, for example in the shape of a plate or disk, provide light confinement in only two dimensions.

In microsphere-based biosensors, antibodies are first immobilized onto the microsphere surface. The subsequent binding of bacteria to antibodies gives rise to an optical transduction signal that can be detected with relevant detectors. One of the challenges in microsphere optical biosensor development is to efficiently deliver bacteria to the sensing surface where binding events occur. Due to the small surface area in microsphere biosensors, a large fraction of bacteria samples will be pumped out of the sensor chamber before they even reach the vicinity of the sphere surface. This is especially true when the sample concentration is low.

Dielectric microspheres have recently drawn increasing attention as fluorosensors in sensing applications. In those sensors, the sensor surface is immobilized with a layer of molecules, such as antibodies, for the subsequent capture of analytes, such as antigens. In a direct assay configuration, antigens are conjugated with fluorescent dye molecules: when the antigen binds with the antibody on the sensor surface, the fluorescent molecule is held sufficiently close to the microsphere surface that it is excited by evanescent light circulating in the microsphere. In a sandwich-type configuration, the antigen is first bound to the antibody on the sensor surface, and then a second layer of antibodies, labeled with a fluorescent dye, is added to bind to the captured antigens. The fluorescent molecules bound to the second layer of antibodies are excited by the evanescent field arising from light propagating in the whispering gallery modes (WGMs) of the microsphere. The resulting fluorescence from the excited dyes is collected and used as an indicator of the antigen binding events.

Optical System

An example of a microcavity-waveguide system 100 that uses a microresonator is schematically illustrated in FIG. 1A. A light source 102 directs probe light along a waveguide 104 to a detector unit 106. The microresonator 110 is optically coupled to the waveguide 104. Probe light 108 from the light source 102 is launched into the waveguide 104 and propagates towards the detector unit 106. The microresonator 110 evanescently couples some of the probe light 108 out of the waveguide 104, the out-coupled light 112 propagating within the microresonator 110 at one of the resonant frequencies of the microresonator 110.

The light source 102 may be any suitable type of light source. For increased efficiency and sensitivity, it is advantageous that the light source produces light that is efficiently coupled into the waveguide 104, for example the light source may be a laser such as a laser diode, or may be a light emitting diode. The light source 102 may also comprise a lamp, along with suitable optics for coupling light from the lamp into the waveguide 104. Some suitable types of light sources are described further in commonly owned U.S. patent application Ser. No. 10/854,911, incorporated herein by reference.

The light source 102 generates probe light 108 at a desired wavelength, or in a desired wavelength range. For example, where the microresonator is used in a sensor, the light source 102 generates light at a wavelength that interacts with the species being sensed. The species being sensed is typically located in proximity to the surface of the microresonator 110 so that the light propagating in the WGM interacts with the species being sensed.

For example, when the system 100 is used as a fluorosensor, the probe light propagating within the microresonator 110 is absorbed by a fluorescent molecule, such as a fluorescent dye, that is attached on the microresonator surface as an analyte or a component of an analyte. In a more specific example, the surface of the microresonator may be attached with antibodies specific to a desired antigen analyte. The analyte antigen molecules, conjugated with a fluorescent dye, are introduced to the sensor system 100. The antigen molecules bind to the antibody molecules on the microresonator 110, thus holding the fluorescent dye molecules sufficiently close to the microresonator 110 that the probe light circulating within microresonator 110 evanescently couples to the fluorescent molecules. The absorbed probe light excites the fluorescent molecules and the molecules subsequently fluoresce at a wavelength different from the probe wavelength. Detection of the fluorescent light confirms the presence of the analyte antigen.

In another example, the analyte antigen molecules are not conjugated with a fluorescent dye, but are allowed to bind to the antibodies attached to the microresonator surface. More antibodies, which may be the same as those attached to the microresonator or may have a different epitope, and which are conjugated to fluorescent molecules, are subsequently introduced to the sensor, and bind to the antigen. Again, the fluorescent molecules are excited by an evanescent interaction with the probe light propagating within the microresonator 110, and detection of the subsequent fluorescence may be used to determine the presence and abundance of the analyte antigen.

The light source 102 may direct probe light into a number of different waveguides, of which the waveguide 104 is one such example. The waveguide 104 may be any suitable type of waveguide and may be, for example, a planar waveguide or a channel waveguide formed in or on a substrate, such as a waveguide formed in a silica substrate. The waveguide 104 may also be an optical fiber.

The detector unit 106 includes a light detector, for example a photodiode or phototransistor, to detect light. The detector unit 106 may also include a wavelength sensitive device that selects the wavelength of light reaching the light detector. The wavelength selective device may be, for example, a filter, or a spectrometer. The wavelength selective device may be tunable so as to permit the user to actively change the wavelength of light incident on the light detector.

The microresonator 110 may be positioned in physical contact with, or very close to, the waveguide 104 so that a portion of the light 108 propagating along the waveguide 104 is evanescently coupled into the microresonator 110. The waveguide 104 typically has little or no cladding at the point where the microresonator 110 couples to the waveguide 104, so that the microresonator 110 couples directly to the core of the waveguide 104.

In some exemplary embodiments, a control unit 116 may be coupled to receive detection signals from the detector unit 106. The control unit 116 may be used to analyze the detection signals and to present to a user an output indicative of the detection signals produced by the detector unit 106. The control unit 116 may include elements typically used in detection systems, such as an amplifier, an analog to digital converter, a buffer, a microprocessor and the like. In some embodiments, such an output might simply be a voltage signal whose amplitude corresponds to the size of the detection signal. In other embodiments, the output may be a digital reading. The control unit is illustrated only in the embodiment shown in FIG. 1A, but it will be appreciated that the control unit may also be employed with any of the exemplary embodiments discussed herein.

Figure 1B:
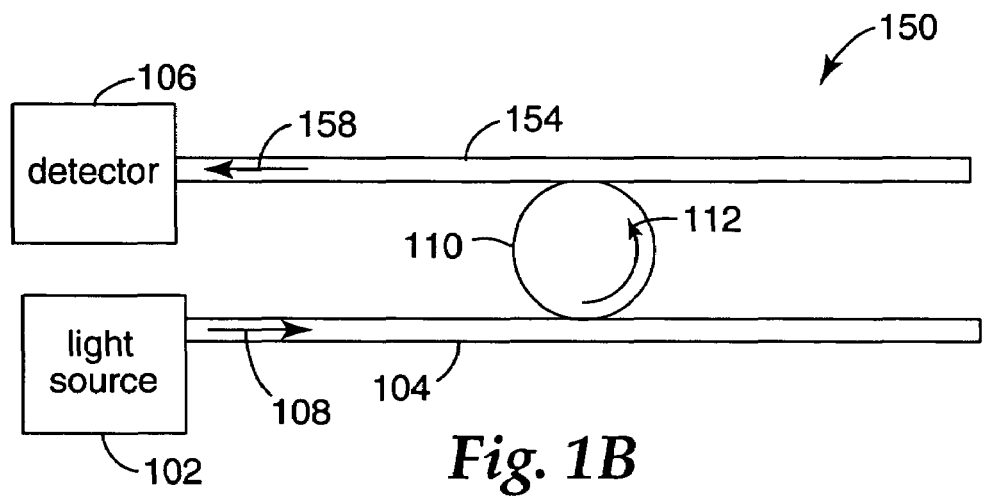

Another type of microresonator device 150 is schematically illustrated in FIG. 1B. In this device 150, signal light 158 from the microresonator 110 is coupled into a second waveguide 154, and propagates to the detector 106.

Figure 1C:
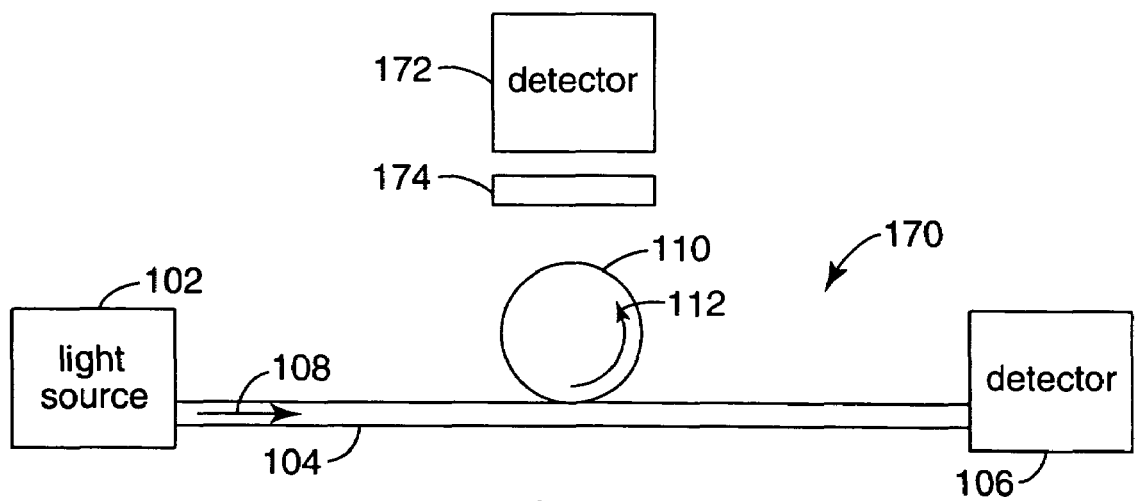

Another type of microresonator device 170 is schematically illustrated in FIG. 1C. In this device 170, a second detector 172 is positioned close to the microresonator 110 to detect light from the microresonator 110. The light detected by the second detector 172 does not pass to the second detector 172 via a waveguide, and is said to propagate through free space. The light from the microresonator 110 that is detected by the second detector 172 may be, for example, scattered out of the microresonator 110 or may be fluorescent light arising from excitation of a fluorescent species, attached to the surface of the microresonator, by light circulating within the microresonator 110. The second detector 172 may detect all wavelengths of light from the microresonator 110 or, for example through the use of a wavelength selective element 174 placed between the second detector 172 and the microresonator 110, may detect light that lies in a specific wavelength range. The wavelength selective element 174 may, for example, be a filter that rejects light at the excitation wavelength resonating within the microresonator 110 and that transmits light at the fluorescent wavelength. The second detector 172 may also be used with a configuration like that shown in FIG. 1B.

Figure 2A:
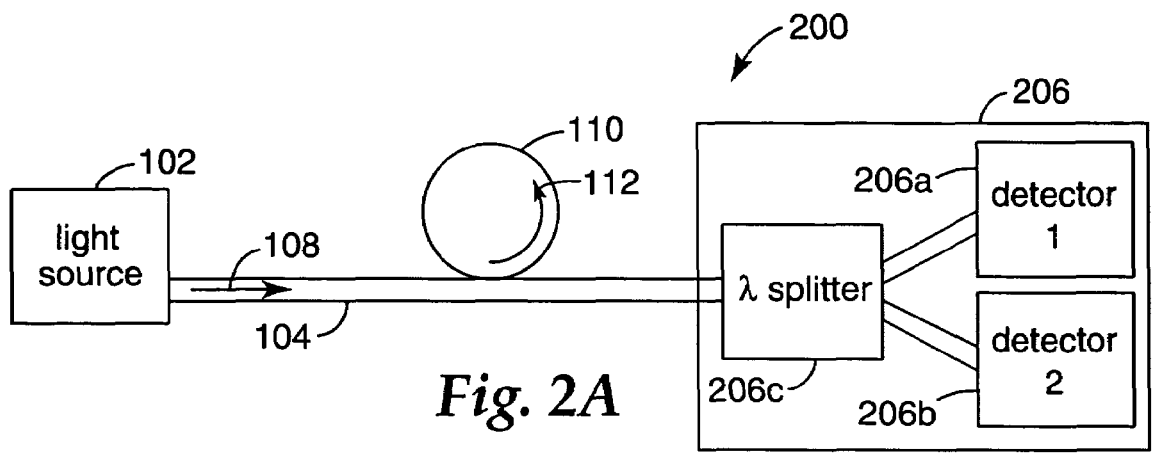
FIGS. 2A–2C schematically illustrate different embodiments of microcavity sensors according to principles of the present invention.
Figure 2B:
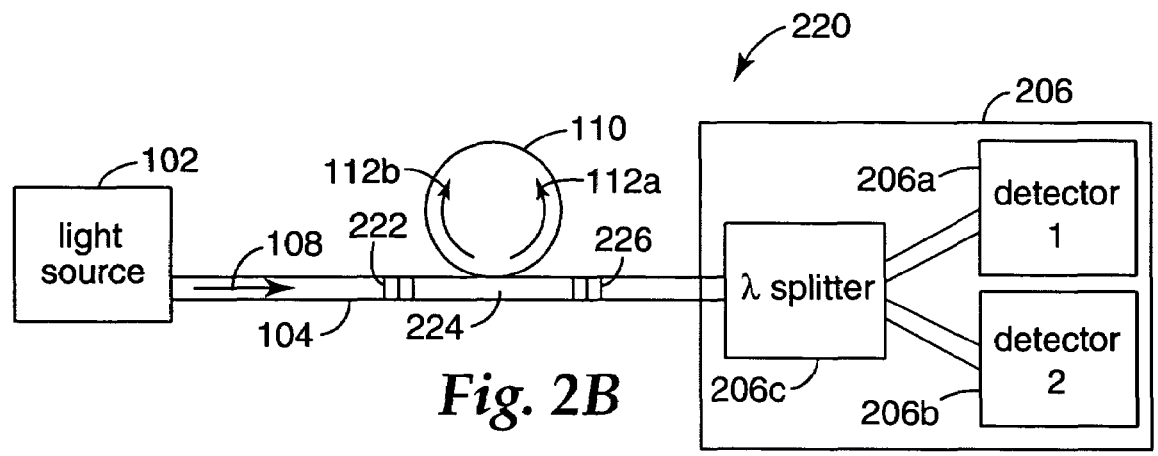

Some other exemplary embodiments of the invention are now discussed with reference to FIGS. 2A–2C. In the exemplary embodiment 200 illustrated in FIG. 2A, the detector unit 206 comprises first and second detectors 206a and 206b. Also, a wavelength-dependent splitter, 206c is used to split light received along the waveguide 104 from the microresonator 110, so that light of one wavelength, or a first range of wavelengths, is passed to the first detector 206a and light at a second wavelength, or second range of wavelengths is passed to the second detector 206b. The wavelength-dependent splitter 206c may use any suitable approach for separating light of different wavelengths. For example, the splitter 206c may employ waveguide-based, wavelength dependent elements such as directional waveguide couplers or Bragg reflectors, or may employ free-space based elements, such as filters, prisms or the like. The values of the first and second wavelengths, or wavelength ranges, may be changed by an operator.

In one example, the first wavelength, or wavelength range, may include the probe light emitted by the light source 102, while the second wavelength, or wavelength range, may include light emitted by an analyte attached to the surface of the microresonator 110. In another example, both the first and second wavelengths, or wavelength ranges, may include light emitted from analyte species attached to the microresonator. This arrangement may be useful, for example, when the analyte material attached to the surface of the microresonator include at least two fluorescing species that emit light at different wavelengths.

The detector unit 206 may also be used in an embodiment, such as is illustrated in FIG. 1B, where the signal light from the microresonator 110 propagates along a second waveguide 154 different from the first waveguide 104. In addition, the detector unit 206 may be used along with another detector that detects light from the microresonator that has propagated through free space.

The waveguide 104 may be provided with one or more reflectors, for example, Bragg gratings, to preferentially reflect light of different wavelengths. For example, as is schematically illustrated in FIG. 2B, a microresonator sensor system 220 may be provided with a waveguide that has a reflector 222 that reflects fluorescent light. Therefore, signal light coupled from the microresonator 110 into the signal coupling region 224 of the waveguide 104 in a direction towards the light source may be reflected by the reflector 222 back towards the detector unit 206. The signal coupling region 224 is that region of the waveguide into which the signal light is coupled from the microresonator. The signal light may be fluorescent light or may be light at the wavelength of the probe light. The use of the reflector 222 may result in an increase in the amplitude of the optical signal detected at the detector unit 206.

A probe light reflector 226, positioned on the waveguide 104 between the signal coupling region 224 and the detector unit 206, may be used to reflect probe light back towards the signal coupling region 224. The second reflector 226 may be used to increase the amount of probe light coupled into the microresonator 110, by introducing a probe component 112b that propagates within the microresonator 110 in a direction opposite to that probe component 112a coupled directly from the light source 102.

Waveguide reflectors may also be used in other configurations. For example, in a configuration as illustrated in FIG. 1B, a reflector for the signal light may be disposed with the second waveguide, to reflect light to the detector unit.

Figure 2C:
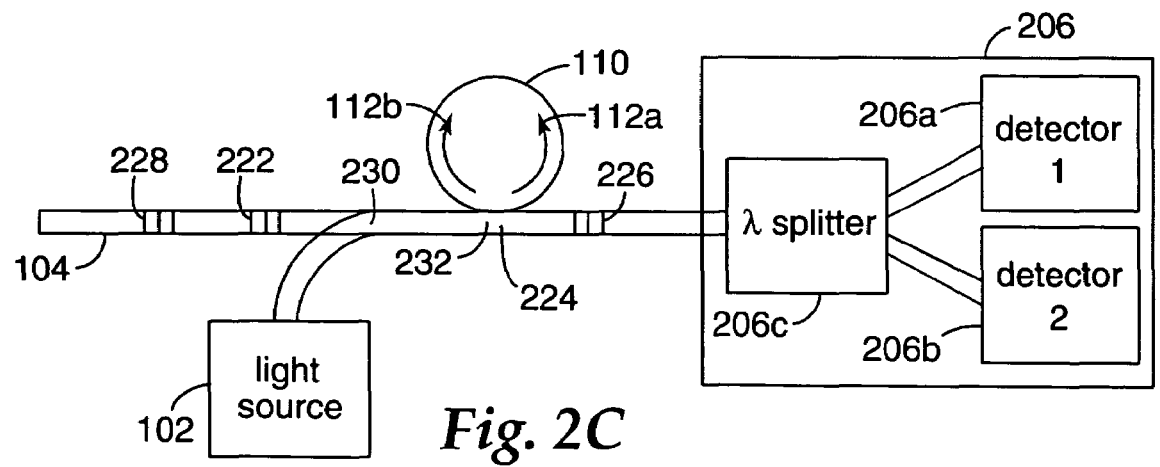

Another configuration is schematically illustrated in FIG. 2C, in which the waveguide 104 is provided with a second probe reflector 228. In this configuration, light from the light source is coupled into the waveguide 104 at a second coupling region 230, for example via a directional coupler, and is coupled into the microresonator at the input coupling region 232. The input coupling region 232 is that region of the waveguide from which probe light is coupled into the microresonator. In the embodiment illustrated, the input coupling region 230 and the signal coupling region 224 substantially overlap. However, where different waveguides are used for the probe light and the signal light, the input coupling region is in one waveguide and the signal coupling region is in another waveguide.

The first probe light reflector 226 reflects probe light from the light source 102 that is not coupled into the microresonator 110. Not all of the reflected probe light is coupled into the microresonator 110 on the return trip, and may therefore be reflected back to the input coupling region 232 by the second probe reflector 228. A resonant cavity may be set up between the two probe reflectors 226 and 228. Depending on some factors, such as the coherence length of the light emitted by the light source 102, and the Q-factor of the resonant cavity, the probe light may resonate between the two probe reflectors, thus increasing the electric field of the probe light at the input coupling region 232, which may further enhance the amount of probe light coupled into the microresonator 110. Under some circumstance of high Q-factors, there may be some mode matching among the modes of the microresonator 110 the modes of the resonant cavity formed by probe reflectors 226 and 228, and the modes of the light source 102, if any. It should also be noted that a broadband laser, for example as discussed in U.S. patent application Ser. No. 10/854,911, may be used as the light source.

Bacterial Detection

Various approaches to bacterial detection may be employed using the sensor system discussed above. For example, the sensor system may be used for the detection of Gram positive and/or Gram negative bacteria. The following is a list of different approaches:

1. Immobilize antibodies or binding molecules against a specific type of bacterium, for example, antibodies against *Staph Aureus*, a common cause for post surgical infection, to the surface of the microsphere and then let the bacteria bind to the antibodies, stain the bacteria with fluorescent dye, and then detect a fluorescent signal from the dye.
2. Immobilize antibodies or binding molecules against a specific type of bacterium, or Gram positive, or Gram negative bacteria, then lyse the bacteria, for example by treating with an enzyme such as lysostaphin or trypsin, and/or in combination with detergents and a salt solution, then let the lysed bacteria bind to the antibodies, stain the bacteria with fluorescent dye, and then detect a fluorescent signal from the dye.
3. Immobilize Gram positive bacteria to the microsphere, stain the bacteria and detect the fluorescent signal resulting from the stain.
4. Immobilize Gram negative bacteria to the microsphere, stain the bacteria and detect the fluorescent signal resulting from the stain.
5. Immobilize antibodies or binding molecules for Gram positive bacteria to the surface of the microsphere, let the Gram positive bacteria bind to the antibodies, optically detect the presence of the Gram positive bacteria.
6. Immobilize antibodies or binding molecules for Gram negative bacteria to the surface of the microsphere, let the Gram negative bacteria bind to the antibodies, optically detect the presence of the Gram negative bacteria.
7. Immobilize antibodies or binding molecules against Gram positive bacteria to the surface of the microsphere, then let the bacteria bind to the antibodies, stain the Gram positive bacteria with fluorescent dye, and then detect fluorescent signal from the dye.
8. Immobilize antibodies or binding molecules against Gram negative to the surface of the microsphere, then let the bacteria bind to the antibodies, stain the Gram negative bacteria with fluorescent dye, and then detect fluorescent signal from the dye.

These different approaches need not be practiced in isolation from each other, and some may be practiced at the same time. For example, if the fluorescent dye indicating Gram positive bacteria emits light of a different wavelength from the fluorescent dye indicating Gram negative bacteria, then a single microsphere could be used to detect the presence of both Gram negative and Gram positive bacteria simultaneously and individually. For example, crystal violet dye is often used to indicate the presence of Gram positive bacteria while basic fuchsin is used to indicate the presence of Gram negative bacteria. A specific antibody may be used to indicate the presence of specific bacteria type.

The first two approaches are now discussed in greater detail. Any of the exemplary optical sensor system embodiments discussed above may be used for this approach. Antibodies against, for example, *Staph Aureus* bacteria, are immobilized on the surface of the microsphere. *Staph Aureus* bacteria are allowed to bind to the bound antibodies. Unbound bacteria are washed away. Fluorescently labeled anti-*Staph Aureus* antibody then are allowed to bind to the bound bacteria, and fluorescence intensity is measured. The intensity of the fluorescent signal may be proportional to the amount of bound bacteria.

Any of the exemplary optical sensor system embodiments discussed above may be used for the third and fourth approaches. Gram positive and negative bacteria are stained or/and counterstained with two different dyes, e.g. crystal violet and basic fuchsin, and are subsequently attached to the surface of a microsphere, for example by air drying or using a small burner. Alternately, the staining may take place following the attachment of the bacteria to the surface of the microsphere.

Since the probe light circulates around the microsphere in a WGM, which lies close to the surface of the microsphere, only the dye molecules in the bacteria adsorbed onto the sphere surface are excited by the probe light and the emitted light subsequently coupled back to the waveguide. At the detection unit, wavelength-selective splitter is used to direct the light at different wavelengths to the different detectors. The light intensity is monitored and calibrated to obtain the number of Gram positive and/or negative bacteria on the microsphere surface.

As was discussed above, the probe light is confined within the WGM of the microsphere sphere for a relatively long time. The local electric field at the microsphere surface is greatly enhanced, compared to the electric field of light making a single pass in the waveguide. A planar micro-disk system with a Q factor of only 5000 can obtain a field multiplication factor of over forty times. A glass microsphere, as discussed herein, can obtain a Q-factor as high as $4 \times 10^6$, with a concomitant further multiplication of the optical field strength.

Fluorescent light from the microsphere can be detected using light that has been guided to the detector unit via a light guide or using light for the microsphere that has propagated in free space, i.e. unguided, for example using a high NA micro-objective placed close to the microsphere surface. While using a microscope objective may have a higher collection efficiency, waveguide-based collection is compact, flexible, low cost, allows for remote sensing, and is simpler. Another approach to collecting the light from the microsphere is to use a lensed fiber placed close to the sphere surface and a dichroic beam splitter is followed to separate the light at different wavelengths. This is also considered to be a free-space technique, since the light undergoes unguided propagation between the microsphere and the lensed fiber.

The evanescent field of the WGM circulating within the microsphere extends to a 1/e distance beyond the surface of the microsphere of about λ/n, where λ is the wavelength of the probe light and n is the refractive index of the medium surrounding the microsphere surface. For light at a wavelength of 600 nm and a surrounding medium of water (n=1.33), the 1/e distance is less than one half of a micron. Since the size of the bacteria attached to the microsphere surface is approximately 1 micron, a significant fraction of the evanescent coupling does not extend beyond the monolayer of bacteria that is in contact with the microsphere surface.

While the total number of bacteria adsorbed onto the microsphere surface may be low, for example, a few thousand, a much higher concentration of dye molecules may be achieved in the cell wall. In other words, multiple dye molecules can be associated with a single bacterium. Therefore, the fluorescent signal from the dye molecules close to the surface of the microsphere may strong enough even for the detection of a single bacterium.

Figure 3:
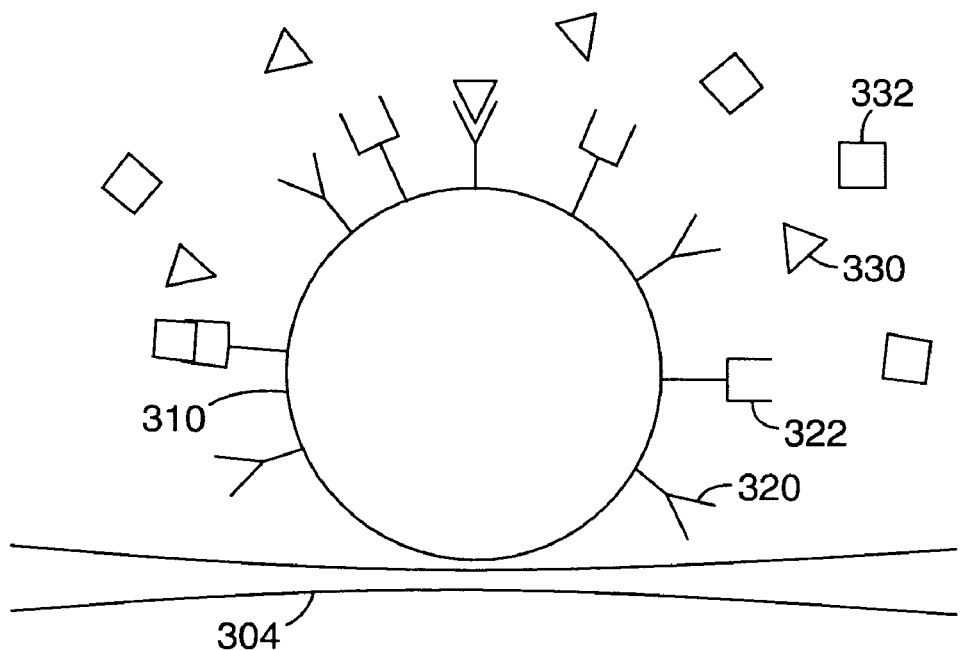
FIG. 3 schematically illustrates an embodiment of a microsphere resonator attached with antibodies for attracting selected bacteria according to principles of the present invention.

In approaches (5)–(8) listed above, antibodies or binding molecules are first immobilized onto the microsphere surface. The subsequent binding of bacteria to antibodies or binding molecules gives rise to optical transduction signal that can be detected with relevant detectors. The use of antibodies or binding molecules is discussed with reference to FIG. 3. A microsphere resonator 310 is optically coupled to a waveguide 304, illustrated as a tapered fiber waveguide. The microsphere is attached with antibodies on its surface. In the illustrated embodiment, there are two different types of antibodies or binding molecules 320, 322, associated with different types of antibodies or binding molecules, although there may only be only one type of antibody or binding molecule or more than two types of antibodies and binding molecules. The first antibody or binding molecule 320 is shown schematically as having a triangular receptor while the second antibody or binding molecule 322 is shown schematically as having a square receptor.

A mixture of different bacteria 330 and 332 surrounds the microsphere resonator, for example in an aqueous solution. The first type of bacterium 330, shown schematically as triangular, becomes attached to the first type of antibody or binding molecule 320. The second type of bacterium 332, shown schematically as square, becomes attached to the second type of antibody or binding molecule 322.

The bacteria 330, 332 may themselves be fluorescent, producing light at a wavelength that is different from the probe wavelength, or may be stained with a dye to provide a fluorescent signal. The bacteria 330, 332 may be stained with the dye before or after attaching to their respective antibodies or binding molecules 320, 322.

Protein Detection:

The above detection approach can also be used for protein detection. In some sense, the detection of bacteria is based on the detection of a protein, since an antibody attaches to a specific protein expressed on the surface of a bacterial cell wall. In addition, a target protein binding molecule or an antibody can be immobilized on a microsphere and used to capture a target protein. More antibodies or binding molecules, which may be the same as those attached to the microresonator or which may have a different epitope, and which are conjugated to fluorescent molecules, can be subsequently introduced to the sensor, and can bind to the target protein. Again, the fluorescent molecules can be excited by an evanescent interaction with the probe light propagating within the microresonator, and detection of the subsequent fluorescence may be used to determine the presence and abundance of the target protein. This approach may provide a device for detecting protein-protein interaction in a cell signaling system. The detection of the protein albumin using a microsphere is described in co-owned U.S. patent application Ser. No. 10/854,911, in which streptavidin labeled with Alexa Fluor 647 dye was used as a label for bovine serum albumin that was attached to a microsphere.

Virus and Spore Detection:

The above detection approach can also be used for the detection of viruses and spores. For example, a binding molecule or an antibody can be immobilized against the microsphere. The binding molecule or antibody can be attached to a virus or spore. More antibodies or binding molecules, which may be the same as those attached to the microsphere or may have a different epitope, and which are conjugated to fluorescent molecules, can be subsequently introduced to the sensor, and can bind to the antigen. The fluorescent molecules can be excited by an evanescent interaction with the probe light propagating within the microresonator, and detection of the subsequent fluorescence may be used to determine the presence and abundance of the target virus or spore. One example of spore detection is the detection of the anthrax spore, which is formed by the bacterium *Bacillus anthracis* and causes an acute infectious disease. Anthrax most commonly occurs in wild and domestic lower vertebrates (cattle, sheep, goats, camels, antelopes, and other herbivores), but it can also occur in humans when they are exposed to infected animals or tissue from infected animals.

DNA Detection:

The above detection approach can also be used for DNA/RNA detection. For example, an oligonucleotide, having a sequence complementary to portions of the sequence of the target nucleic acid is immobilized on the microsphere surface. An unlabeled oligonucleotide detection scheme may be used, or a DNA/RNA intercalation dye can be incorporated, and the detection will be conducted in the fluorescent detection mode.

Example—Bacterial Detection Using Microsphere

A microsphere attached with a bacterial sample was prepared using the following technique. A silica glass microsphere, approximately 150 μm in diameter, was treated with a Piranah solution for 5 min, and then rinsed with purified water. The Piranah solution was a 3:1 mixture of concentrated sulfuric acid ($H_2SO_4$) with hydrogen peroxide ($H_2O_2$). The sulfuric acid was supplied by Mallinckrodt Baker, Inc, Phillipsburg, N.J. The hydrogen peroxide was obtained in a 30% solution from Mallinckrodt Laboratory Chemicals, Phillipsburg, N.J. The cleaned glass microsphere was removed from water. The microsphere was then placed into an ethanol solution containing 0.5% of 3-mercaptopropyl trimethoxysilane, supplied by Fluka, Buchs, Switzerland. The reaction was allowed to proceed for 5 minutes at room temperature. The microsphere was removed from the silane solution, and rinsed with ethanol twice, air dried, and then placed in a reaction vessel that contained 1.1 mM solution of N-succinimidyl-4-maleimidobutyrate (GMBS), supplied by Pierce Chemical Company, Rockford, Ill. The microsphere was incubated with the GMBS solution for 5 minutes, and then rinsed with ethanol.

A solution of anti-*Staph Aureus* antibody was prepared in phosphate-buffered saline (PBS) at a concentration of 0.1 mg/ml. The anti-*Staph Aureus* was a polyclonal antibody to

*staphylococcus aureus* and was supplied by Accurate Chemical & Scientific Corporation, Westbury, N.Y. The PBS was supplied as a 10× liquid concentrate by EMD Chemicals, Gibbstown, N.J. The microsphere was incubated with this solution for 5 minutes.

The microsphere was then blocked with 2 mg/ml bovine serum albumin (BSA), supplied by Sigma Aldrich, St. Louis, Mo., in PBS with 0.1% Tween 20, polyoxyethylenesorbitan monolaurate supplied by Sigma Aldrich, St. Louis, Mo., for 5 min. Subsequently, a *Staph Aureus* bacteria solution, bacteria strain 25923, American Type Culture Collection, Manassas, Va., and having a concentration of $10^7$ cells/ml, was allowed to incubate with the microsphere for 5 minutes, to permit the bacteria to attach to the microsphere. Finally, anti-*Staph Aureus* antibody, labeled with Alexa Fluor 647, supplied by Molecular Probes, Eugene, Oreg., at a concentration of 10 μg/ml was incubated with the microsphere. This resulted in a microsphere that was attached with *Staph Aureus* bacteria labeled with Alexa Fluor 647 dye.

A flow chamber was built by epoxying glass slides together. Polymer tubing was glued in place, also using epoxy, to serve as input and output paths. The silanization and GMBS treatment was done as described above. The subsequent steps were performed in the flow chamber.

A control microsphere was produced using the same steps as listed above, except that microsphere was incubated with PBS instead of incubating the microsphere with the bacteria solution.

The sample microsphere and the control microsphere were used as microresonators in an optical biosensing system. The experimental setup was similar to that illustrated in FIG. 1C, in which the light source directed light in the range of 630–635 nm through a tapered fiber as the coupling waveguide. The fiber core tapered to a diameter of around 1.5 μm–2.5 μm. A first detector was positioned to detect light that had passed along the waveguide, past the microsphere. A second detector was positioned to detect the free space emission of light from the microsphere.

The microcavity was illuminated with light coupled from a laser diode that had an output at 635 nm and an output bandwidth of 0.5 nm (500 μm). The optical power coupled into the fiber taper was approximately 250 μW.

Figure 4:
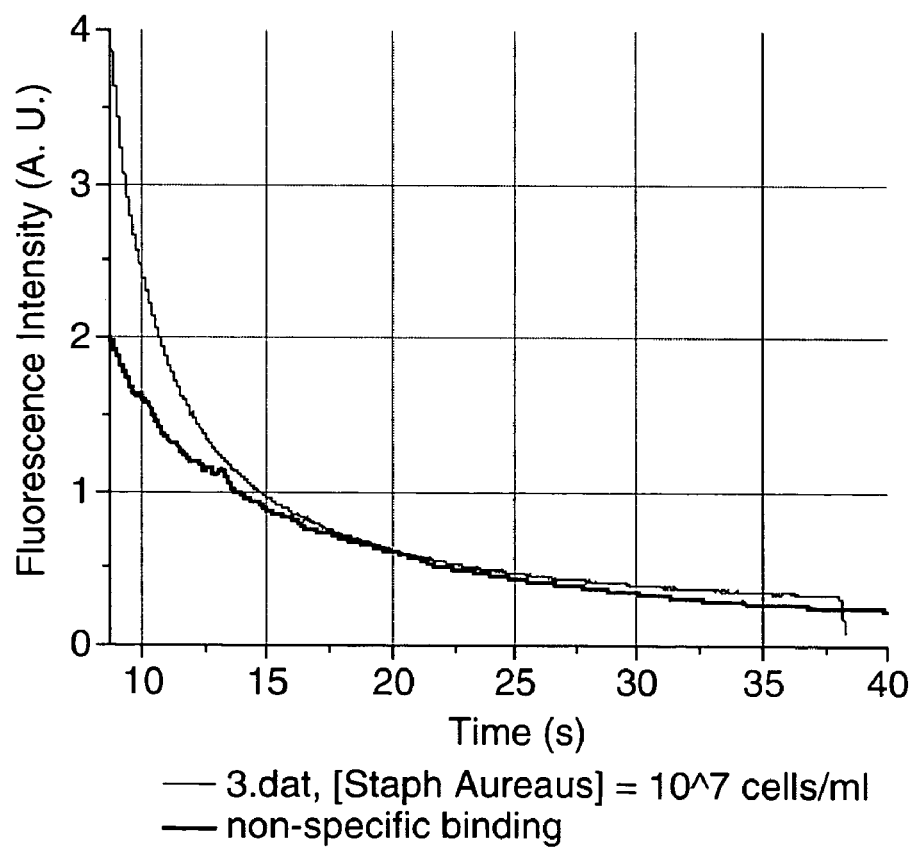
FIG. 4 presents a graph showing fluorescence activity as a function of time.

The fluorescent responses, as detected by the second, free space detector, of the *Staph*-attached microsphere and the control microsphere are illustrated in FIG. 4 as a function of time. In each case, the excitation light was initially blocked at the input to the tapered fiber, so that no light was coupled into the microsphere. At time t=8 seconds, the excitation light was unblocked, and fluorescent signals were observed. This corresponds to the fluorophore emitting light as a result of being excited by light resonant in the microsphere. The light from the laser diode was chopped and the fluorescent signal detected using a lock-in amplifier. After approximately 25–35 sec of excitation time, the fluorescent signal had fallen to a low level. This reduction in signal strength over time was attributed to bleaching of the dye molecules.

The initial fluorescent signal of the *Staph*-attached microsphere is initially about double that of the control sample, demonstrating that the specific binding of the dye to the *Staph* bacteria produces a significant optical effect.

One of the challenges with microsphere optical biosensors is to efficiently deliver the target to the sensing surface where the binding events occur. Since the surface area of a microsphere is small, a large fraction of the target in solution may not even reach the vicinity of the sphere surface before being removed from the chamber. This is particularly a problem when the sample concentration is low.

Figure 5A:
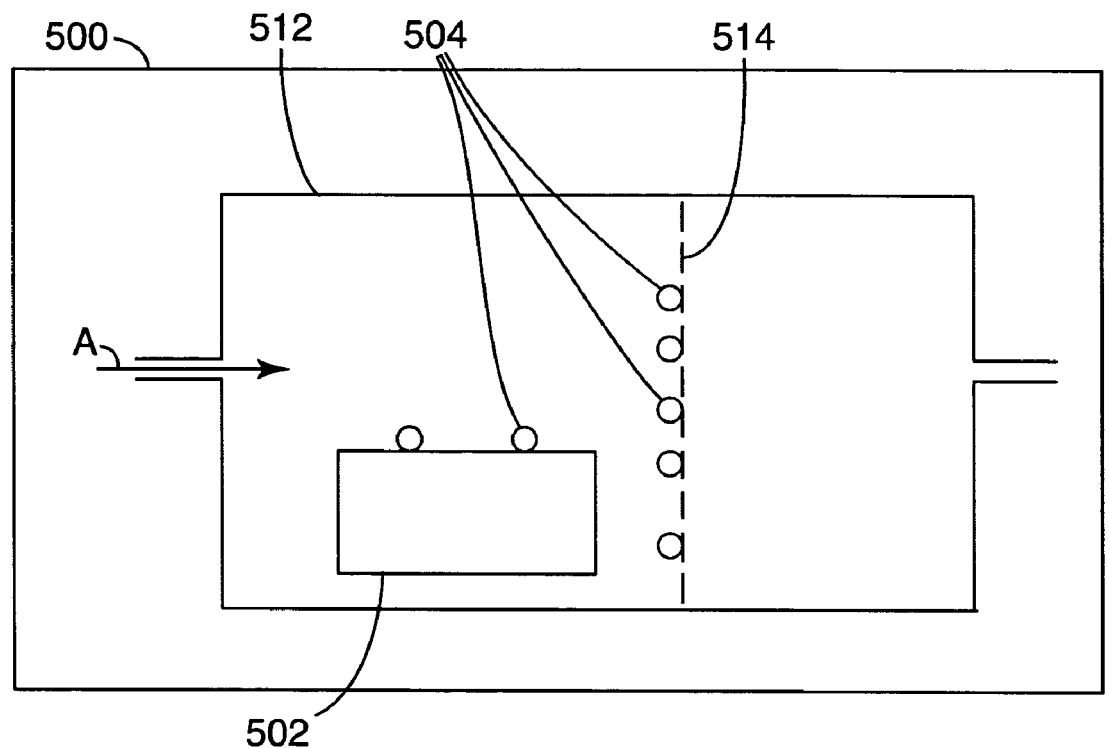
FIGS. 5A–5C schematically illustrate embodiments of bacterial sensor systems according to principles of the present invention.
Figure 5B:
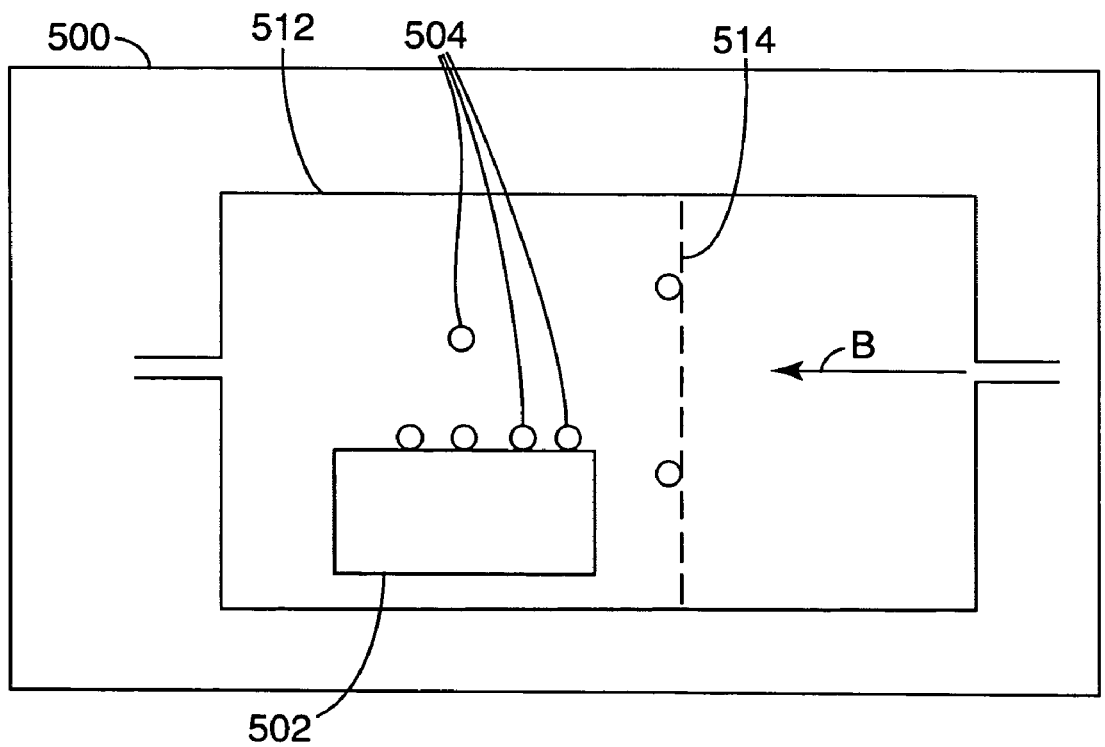
Figure 5C:
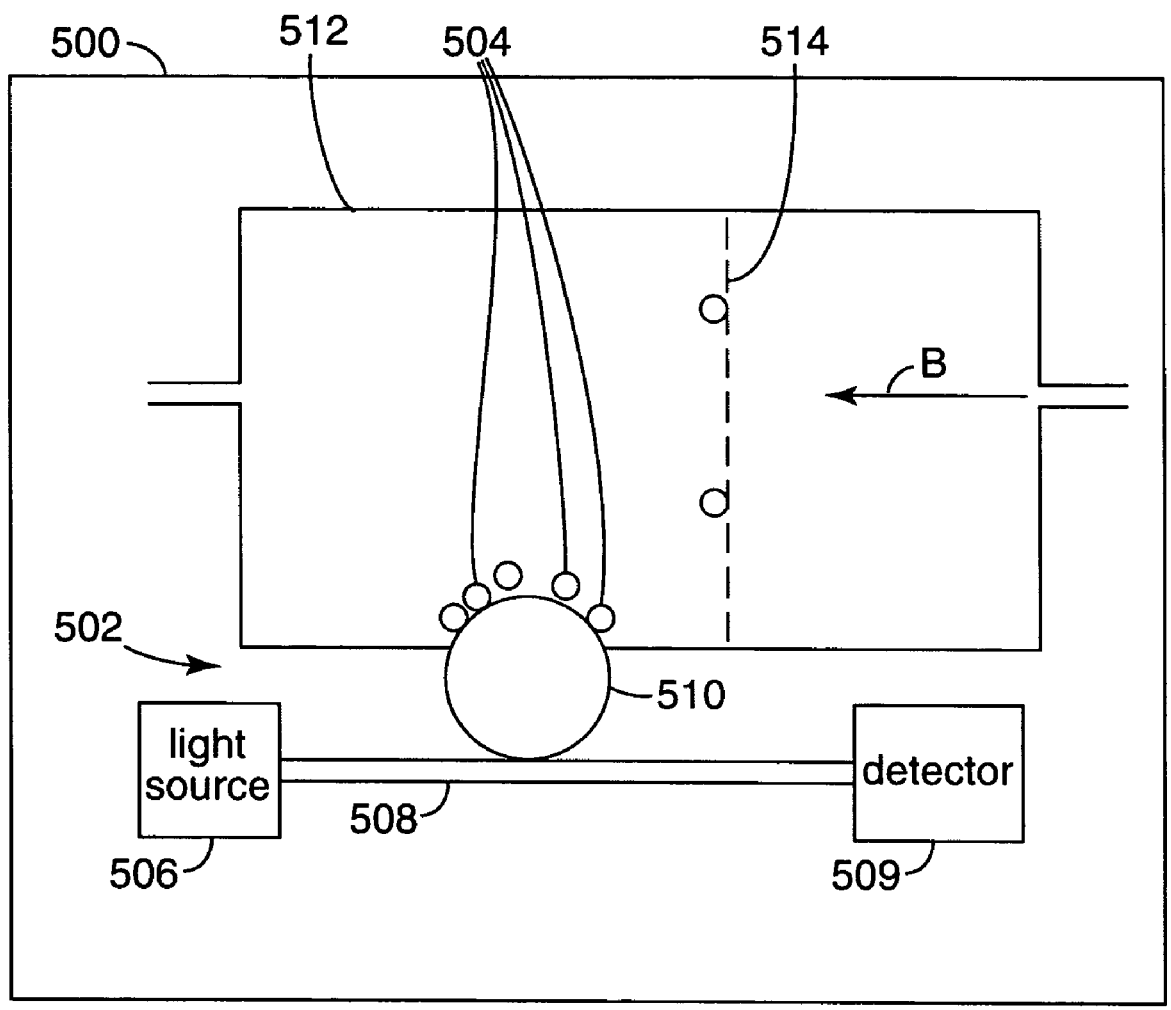

Accordingly, it is useful to increase the effective concentration of the target in the solution. This concentration increase may be achieved using a filter disposed close to microsphere sensor surface is mounted in the distant end of the sensor chamber. An exemplary embodiment of a biosensor system is schematically shown in FIGS. 5A–5C. The system 500 includes a sensor unit 502 disposed within a chamber 512 which has a filter 514 at one end. The filter 514 has a pore size appropriate for trapping the target being sensed and may have a pore size, for example, of up to 2 μm, up to 1 μm, up to 0.8 μm, and/or up to 0.45 μm. In some cases, for example where the system is being used to sense protein molecules or fragments of DNA or RNA, the filter may be a molecular filter. Such filters have even smaller pores, for example in the range of about 5 nm–10 nm and may be designed to trap molecules having a molecular weight above a specific value, for example 10,000. In addition, different types of pumps may be used when the solution is passed through a filter with such small pores.

The sensor unit 502 comprises a biosensor, for example an optical biosensor based on microspheres as discussed above, or may be some other type of biosensor, such as a biosensor based on surface acoustic waves (SAW), and further described in co-owned U.S. provisional patent application Ser. Nos. 60/533169 and 60/533176, incorporated herein by reference.

The sample containing the target analyte is introduced to the sensing chamber 512, generally in the direction indicated by the arrow "A", for example using a syringe or a pump, such as a peristaltic pump. The sample washes by the sensor unit 502, and some of the target analyte 504 attaches to the active surface of the sensor unit 502. In the case of a microsphere-based biosensor, the active surface is the surface of the microsphere, which may be provided with antibodies or binding molecules appropriate to the target bacteria, protein, spore, virus or DNA/RNA being sensed. Most of the target analyte 504 that does not initially attach to the sensor unit 502 is trapped by the filter 514 as the solution passes through the chamber 512. A subsequent backflow, generally in the direction marked with the arrow "B", as schematically illustrated in FIG. 5B, is then applied to recover the target analyte from the filter 514 and to wash the target analyte 504 past the sensor unit 502 once more. More analyte attaches to the active surface of the sensor unit 502 in the backflow. Where the sensor unit 502 is immobilized with a particular type of antibody or binding molecule, the analyte 504 of interest can be captured, leaving the unbound, and therefore unselected, species to be washed away by the backflow.

The entire sensor unit 502 need not be present within the chamber 512. For example, where the sensor unit 502 includes an optical biosensor having a microcavity resonator, the microcavity resonator presents the active surface for trapping bacteria, and so only the microcavity resonator 510, or part of the microcavity resonator, may be present in the chamber 512, as is schematically illustrated in FIG. 5C. The light source 506 generating the light that couples to the microcavity resonator 510, the waveguide 508 coupling light from the light source 506 to the microcavity resonator 510, the detector unit 509 and any waveguide coupling light from the microsphere to the detector unit 509, waveguide 508 in the illustrated embodiment, need not be located within the sensing chamber 512. This permits the sensing chamber 512 to be small, for example, with dimensions of the same order as those of the microcavity resonator 510. It will be appreciated, however, that some elements of the sensor unit 502 need not be restricted from the sensing chamber. For example, the microcavity resonator 510 may be located entirely within the chamber 502, with one or more waveguides passing light into and out of the chamber 502 for coupling to and from the one or more waveguides coupling light to and from microresonator cavity 510, with the light source 506 and detector unit 509 located outside the sensing chamber 512.

Likewise, with other types of biosensors, only a sensing surface may be present in the chamber 512, while other elements of the biosensor may be positioned outside the chamber 512. The backflow may be created using any suitable method, for example by injecting a solution into the chamber 512 using a syringe or by a pump. Furthermore, the same device used to inject the sample into the chamber may be also be used to create a backflow. For example, if a pump is used to direct the sample into the chamber 512, then the pump may be reversed to initiate a backflow. Peristaltic pumps, for example, are well suited to inducing a reverse flow. Other types of pumps may also be used.

The method of filtration capture method can be used to significantly increase the effective concentration of the target analyte, which is especially useful when the dimension of the sensor chamber is relatively small. For example, a microsphere used in an optical biosensor typically has a diameter on the order of 100 μm–200 μm. The sensor chamber in which the microsphere is located may, therefore, have a volume on the order of 1 mm³ or less. The concentration effects of a filter may be significant: the concentration ratio, R may be described by the expression:

$$R = (V/C) \times R_C \times R_B \quad (1)$$

where V is the sample volume that flows through the chamber, C is the chamber volume, $R_C$ is the capture ratio of the filter, i.e. the percentage of the target analyte captured in by the filter in the forward flow, typically about 100% for a properly designed filter, and $R_B$ is the recovery ratio from the filter, i.e. the fraction of the captured analyte that is washed off the filter back into the chamber in a backflow.

In an exemplary embodiment in which the target analyte is bacteria, the chamber size, C, is 1×1×1 mm ($10^{-3}$ ml). If a 1 ml in-flow (V=1 ml), with a concentration of 100 cells/ml, passes through the chamber, and the filter captures 100% of the bacteria, then the filter traps 100 bacteria. If the backflow recovery ratio is 20%, then 20 cells can be restored to the chamber from the filter, producing a cell concentration of 2×10⁴ cells/ml. Thus, the use of the backflow filter technique can result in an increased effective sample concentration, and lead to increased sensitivity.

The filtration capture method may be more rapid, inexpensive, and readily scaled up to larger volumes than other methods, such as magnetic particle concentration. Furthermore, the filtration capture method need not be limited to microsphere-based biosensors, and may be used with other types of sensors, such as surface acoustical wave (SAW) sensors.

Examples—Filtration Capture

A number of experiments using *Staph Aureus* as a model system have been performed to explore the filtration capture technique and its suitability for use in an optical biosensing system. The concentration of *Staph Aureus* in Tris buffered saline ranges from $10^7$ cells/ml to $10^4$ cells/ml. The filters were polycarbonate and cellulose acetate filter membranes, having pore sizes of 0.45 μm, 0.8 μm, or 1 μm are used. During each experiment, two parameters were monitored, namely i) capture efficiency, that is the number of bacteria that were blocked by the filter, and ii) the recovery ratio, that is the fraction of total bacteria that could be recovered from the filter by the backflow. Furthermore, for the recovery ratio measurements, a 1 ml backflow was used five times sequentially, and the recovery ratio was recovered after each backflow.

When the cell concentration was $10^7$ cells/ml, the quantitation was performed using a fluorescence detection method with a fluorimeter. The fluorescence detection method was not sufficiently sensitive when the concentration was $10^4$ cells/ml, and so a bacteria culturing and counting method was used instead.

Experiment A—Recovery Ratio High Concentration

Initially, a *Staph Aureus* solution having a concentration of $10^7$ cells/ml was prepared. The filter size is 47 mm in diameter with either a 1 μm pore-size polycarbonate filter or a 0.8 μm pore size cellulose acetate filter. Table I lists the recovery ratio of the *Staph Aureus* after 5 times of 1 ml backflow.

TABLE I

*Staph Aureus* concentration = $10^7$ cells/ml.

| Filter | Recovery |
| --- | --- |
| Polycarbonate 1 μm pore | ~100% |
| Cellulose Acetate 0.8 μm pore | ~100% |

Thus, at concentrations of $10^7$ cells/ml, the recovery is almost complete.

Experiment B—Recovery Ratio, Low Concentration

At lower concentrations, however, the recovery ratio is less than when the concentration is $10^7$ cells/ml. For example, at a concentration of $10^4$ cells/ml, the recovery ratio fell to 24%. This reduction in recovery ratio was attributed, at least in part, to the dead volume caused by the adsorption of bacteria to the filter membrane. It was found that the recovery ratio increased when filters with a smaller area were used. For example, when the filter diameter was reduced to 13 mm, the recovery ratio increased to 53% (on average for three experiments, see Tables II–IV below). It should be noted that in actual microsphere biosensor chambers, the filter diameter may be as small as 1 mm, resulting in an even smaller dead volume, and increased recovery ratio.

Tables II–IV show the recovery results for each 1 ml backflow when the *Staph Aureus* concentration is varied with a value of about $10^4$ cells/ml. For these experiments, the filters were Acrodisc® syringe filters, available from Gellman Instrument Co., Ann Arbor, Mich. The filters were 13 mm in diameter and were formed from hydrophilic polypropylene membranes having a 0.45 μm pore size. The capture efficiency, not listed in the tables below, remained at about 100%. After the filter had trapped the bacteria, each filter was subjected to repeated backflows of 1 ml each. After each backflow, the solution was removed and cultured to count the bacteria removed from the filter by the backflow. The total recovery ratio after 5 times of 1 ml backflow exceeds 40%. Each table lists the number of cells recovered in each backflow step, along with the percentage of the total cell count that number represents. The bottom row of each table shows a total number for the cells recovered, obtained by summing the numbers in the second column, and shows the total percentage of cells recovered.

TABLE II

Staph Aureus concentration = 9400 cells/ml

| Reverse Fraction | No. of cells | Recovery % |
| --- | --- | --- |
| 1 | 3435 | 36.5 |
| 2 | 834 | 8.9 |
| 3 | 1448 | 15.4 |
| 4 | 169 | 1.8 |
| 5 | 779 | 8.3 |
| Total | 6665 | 70.9 |

TABLE III

Staph Aureus concentration = 12000 cells/ml

| Reverse Fraction | No. of cells | Recovery % |
| --- | --- | --- |
| 1 | 1890 | 15.8 |
| 2 | 680 | 5.7 |
| 3 | 1220 | 10.2 |
| 4 | 313 | 2.6 |
| 5 | 1560 | 13 |
| Total | 5663 | 47.2 |

TABLE IV

Staph Aureus concentration = 12600 cells/ml

| Reverse Fraction | No. of cells | Recovery % |
| --- | --- | --- |
| 1 | 1238 | 9.8 |
| 2 | 630 | 5.0 |
| 3 | 1140 | 9.0 |
| 4 | 200 | 1.6 |
| 5 | 1908 | 15.1 |
| Total | 5116 | 40.6 |

Thus, the backflow recovery was at least 40% when the filter was subjected to five backflows. This confirms that the backflow capture technique may be used to effectively increase the sample concentration for presentation to a sensor.

Accordingly, the present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the present specification. The claims are intended to cover such modifications and devices.

We claim:

1. An optical biosensor system, comprising:

A sensing chamber having an interior volume;

An optical biosensor unit operatively coupled to the interior volume of the sensing chamber, the optical biosensor unit detecting the presence of an analyte;

Said optical biosensor unit further comprising a microcavity resonator with an outside surface, at least part of the outside surface of the microcavity resonator being exposed to the interior volume of the chamber, A filter for trapping target analytes disposed within the sensing chamber; and An input to the sensing chamber for introducing an analyte solution into the sensing chamber, the input being arranged and configured so that at least some of the solution interacts with the optical biosensor unit before reaching the filter.

2. A system as recited in claim 1, further comprising a light source optically coupled to inject probe light into the microcavity resonator.

3. A system as recited in claim 1, further comprising an optical detector unit optically coupled to detect fluorescent light from an analyte attached to an outside surface of the micro cavity resonator.

4. A system as recited in claim 3, wherein the optical detector unit is optically coupled to the microcavity resonator via an optical waveguide.

5. A system as recited in claim 3, wherein the optical detector unit is disposed proximate the microcavity resonator so as to detect signal light that has propagated through free space from the microcavity resonator.

6. A system as recited in claim 3, further comprising a control unit coupled to receive detection signals from the optical detection unit, the control unit analyzing the detection signals.

7. A system as recited in claim 1, wherein the filter has a pore size is no greater than 2 μm.

8. A system as recited in claim 1, wherein the filter has a pore size is no greater than 1 μm.

9. A system as recited in claim 1, wherein the filter has a pore size is no greater than 0.8 μm.

10. A system as recited in claim 1, wherein the filter has a pore size is no greater than 0.45 μm.

11. A system as recited in claim 1, wherein the biosensor unit is adapted and configured to detect a bacterial analyte.

12. A system as recited in claim 1, wherein the biosensor unit is adapted and configured to detect a protein analyte.

13. A system as recited in claim 1, wherein the biosensor unit is adapted and configured to detect a viral analyte.

14. A system as recited in claim 1, wherein the biosensor unit is adapted and configured to detect a spore analyte.

15. A system as recited in claim 1, wherein the biosensor unit is adapted and configured to detect a DNA or RNA analyte.

16. A method of operating an optical biosensor, comprising:

(a) placing a solution containing an analyte into a sensing chamber containing at least a surface of an optical biosensor and a filter for trapping target analytes;

(b) washing the solution past the at least a surface of the optical biosensor to a filter and trapping at least some of the analyte at the filter;

(c) washing at least some of the trapped analyte off the filter back towards the surface of the biosensor; and (d) detecting the analyte on the surface of the biosensor;

Wherein the surface of the optical biosensor comprisies at least part of a microcavity resonator, and detecting analyte on the surface of the optical biosensor comprises detecting an optical signal indicating the presence of the analyte attached to the surface of the microcavity resonator in a sensing chamber having an interior volume.

17. A method as recited in claim 16, wherein washing at least some of the trapped analyte comprises washing analyte trapped by the filter towards the microresonator cavity.

18. A method as recited in claim 16, wherein washing the solution comprises moving the solution with a pump.

19. A method as recited in claim 16, wherein detecting the analyte comprises detecting a bacterial analyte on the at least a surface of the biosensor.

20. A method as recited in claim 16, wherein detecting the analyte comprises detecting a viral analyte on the at least a surface of the biosensor.

21. A method as recited in claim 16, wherein detecting the analyte comprises detecting a protein analyte on the at least a surface of the biosensor.

22. A method as recited in claim 16, wherein detecting the analyte comprises detecting a spore analyte on the at least a surface of the biosensor.

23. A method as recited in claim 16, wherein detecting the analyte comprises detecting a DNA or RNA analyte on the at least a surface of the biosensor.

* * * * *

UNITED STATES PATENT AND TRADEMARK OFFICE
CERTIFICATE OF CORRECTION

PATENT NO. : 7,257,279 B2
APPLICATION NO. : 10/945327
DATED : August 14, 2007
INVENTOR(S) : Chunmei Guo Page 1 of 2

It is certified that error appears in the above-identified patent and that said Letters Patent is hereby corrected as shown below:

Item 56 Page 2, Column 1 (Other Publications)
Line 19, delete "Flouoroimmunsensor" and insert -- Fluoroimmunosensor --, therefor.
Line 22, before "University" delete ";" and insert -- , y --, therefor.
Line 26, delete "Measurement" and insert -- Measurements --, therefor.
Line 27, delete "Microsphers" and insert -- Microspheres --, therefore.
Line 27, delete "Letter" and insert -- Letters --, therefor.

Item 56 Page 2, Column 2 (Other Publications)
Line 1, delete "Subtrate" and insert -- Substrate --, therefor.
Line 13, delete "(TEo)" and insert -- $(TE_o)$ --, therefor.
Line 23, delete "microcavity" and insert -- Microcavity --, therefor.
Line 33, delete "Conmmunications" and insert -- Communications --, therefor.
Line 43, delete "Siicon" and insert -- Silicon --, therefor.

Item 56 Page 3, Column 1 (Other Publications)
Line 18, delete "Mircocavity" and insert -- Microcavity --, therefor.
Line 26, after "et al." delete "," and insert -- ; --, therefor.

Item 56 Page 3, Column 2 (Other Publications)
Line 8, delete "hexgonal" and insert -- hexagonal --, therefor.
Line 14, delete "Microactivities" and insert -- Microcavities --, therefor.
Line 17, delete "Microactivities" and insert -- Microcavities --, therefor.
Line 19, delete "Microactivities" and insert -- Microcavities --, therefor.

Column 7
Line 20, after "Bacterial Detection" insert -- : --.

Column 11
Line 8, delete "polyoxythylenesorbitan" and insert -- polyoxyethylenesorbitan --, therefor.
Line 16, after "Eugene" delete ",".
Line 41, delete "(500 µm)" and insert -- (500 pm) --, therefor.

Column 14
Line 13, after "Recovery Ratio" insert -- , --.

UNITED STATES PATENT AND TRADEMARK OFFICE
CERTIFICATE OF CORRECTION

PATENT NO. : 7,257,279 B2
APPLICATION NO. : 10/945327
DATED : August 14, 2007
INVENTOR(S) : Chunmei Guo It is certified that error appears in the above-identified patent and that said Letters Patent is hereby corrected as shown below:

Column 15
Line 58, in Claim 1, delete "A" and insert -- a --, therefor.
Line 59, in Claim 1, delete "An" and insert -- an --, therefor.
Line 62, in Claim 1, delete "Said" and insert -- said --, therefor.
Line 65, in Claim 1, after "chamber" delete "," and insert -- ; --, therefor.
Line 66, in Claim 1, delete "A" and insert -- a -- , therefor.

Column 16
Line 1, in Claim 1, delete "An" and insert -- an -- , therefor.
Line 12, in Claim 3, delete "micro cavity" and insert -- microcavity --, therefor.
Line 56, in Claim 16, delete "Wherein" and insert -- wherein --, therefor.
Line 56, in Claim 16, delete "comprisies" and insert -- comprises --, therefor.

Signed and Sealed this

Twenty-fifth Day of December, 2007

JON W. DUDAS
*Director of the United States Patent and Trademark Office*